Figure 1:
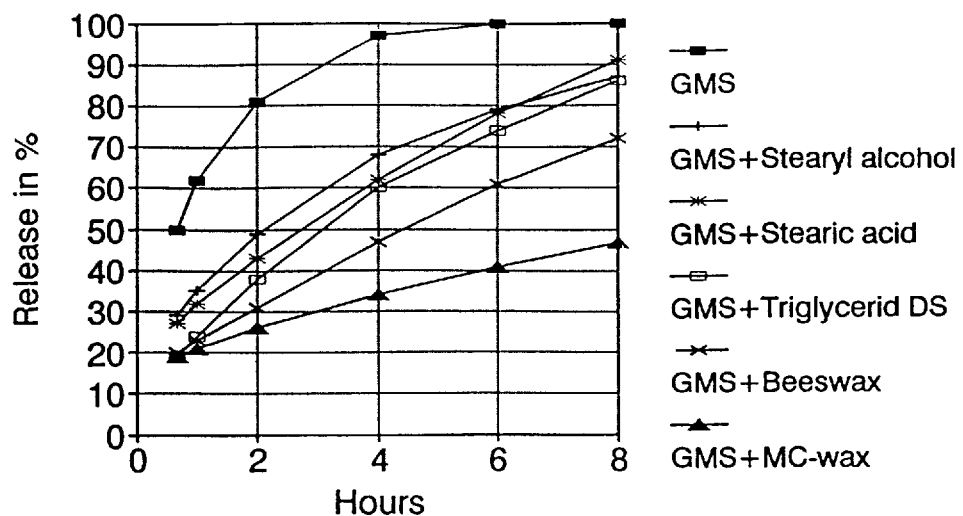

United States Patent

Kristensen et al.

[11] Patent Number: 5,807,583
[45] Date of Patent: Sep. 15, 1998

[54] PROCESS FOR THE PREPARATION OF SUSTAINED RELEASE PELLETS

[75] Inventors: Henning Kristensen, Vedbaek; Torben Schaefer, Hvalsø; Lars Juul Thomsen, deceased, late of Vildbjerg, all of Denmark, by Jorgen Moller Thomsen and Marie Thomsen, heirs; Arne Kristensen, Uppsala, Sweden

[73] Assignee: Pharmacia AB, Uppsala, Sweden

[21] Appl. No.: 307,629
[22] PCT Filed: Mar. 16, 1993
[86] PCT No.: PCT/SE93/00225
§ 371 Date: Jan. 12, 1995
§ 102(e) Date: Jan. 12, 1995
[87] PCT Pub. No.: WO93/18753
PCT Pub. Date: Sep. 30, 1993

[30] Foreign Application Priority Data

Mar. 20, 1992 [SE] Sweden .................................. 9200858

[51] Int. Cl.$^6$ ..................................................... A61K 9/14
[52] U.S. Cl. .......................... 424/489; 424/464; 424/468; 424/461
[58] Field of Search ................... 424/488, 489, 424/490

[56] References Cited

U.S. PATENT DOCUMENTS

| | | | |
|---|---|---|---|
| 4,013,784 | 3/1977 | Speiser | 424/502 |
| 4,132,753 | 1/1979 | Blichare et al. | 264/25 |
| 4,935,246 | 6/1990 | Ahrens | 424/502 |
| 5,008,112 | 4/1991 | DePrince et al. | 424/468 |
| 5,023,089 | 6/1991 | Sakamoto et al. | 424/498 |
| 5,030,400 | 7/1991 | Danielsen et al. | 264/101 |
| 5,358,560 | 10/1994 | Hitch et al. | 106/499 |

FOREIGN PATENT DOCUMENTS 06679 4/1992 WIPO .

OTHER PUBLICATIONS

Schaefer et al, Drug Development and Industrial Pahrmacy, 16(8), pp. 1249–1277 (1990).
Ghali et al, Drug Development and Industrial Pharmacy, 15(9), pp. 1311–1328 (1989).

Primary Examiner—Thurman K. Page
Assistant Examiner—William E. Benston, Jr.
Attorney, Agent, or Firm—Birch, Stewart, Kolasch & Birch, LLP

[57] ABSTRACT

A process for the manufacture of sustained release pellets comprising pelletizing a mixture containing the drug in finely divided form and a binder. The characteristic feature is that:

(a) said binder is in particle form consisting of one or more water-insoluble wax-like binder substance(s) with a melting point above 40° C., and (b) said pelletization step is performed by mechanically working said mixture, in a high shear mixer, under the input of a sufficient amount of energy for the binder to melt and pelletization to take place.

4 Claims, 3 Drawing Sheets

1

PROCESS FOR THE PREPARATION OF SUSTAINED RELEASE PELLETS

This application is a 371 of PCT/SE93/0025 filed Mar. 16, 1993.

TECHNICAL FIELD OF THE INVENTION

The present invention relates to the manufacture of pellets having defined and sustained release characteristics and their multiple unit dose formulations.

The term "pellets" will forthcomingly refer to spherical or spheroidal particles having diameters ranging from 0.2–2.5 mm.

By "multiple unit dose formulation" is contemplated an oral dose formulation that at the appropriate location in the gastrointestinal tract, usually the stomach or intestines makes available a high number of similar units (e.g. pellets or granules).

DESCRIPTION OF THE PRIOR ART

In the field of pharmaceutical development, it is generally agreed that the oral administration of a multiple unit dose formulation possessing a sustained release of the drug substance is beneficial compared to conventional tablet formulations having similar release properties. The benefits of multiple unit dose formulations are primarily that the transport and distribution of the free units in the various segments of the gastrointestinal tract are more uniform and reproducible than single unit dosage forms.

With respect to tablets one has successfully obtained the desired release properties by coating the tablets with wax-like substances or mixes thereof, or by embedding the drug substance in a matrix of binder of different degree of hydrophilicity/hydrophobicity, if necessary together with auxiliary substances like fillers, buffering substances etc.

With respect to granulation/pelletization of powdery drugs the more common techniques are:

(i) Coating inert particles ("non-pareilles"=placebo pellets) with a solution or suspension that contains an active substance, binder and water. The amount of active substance in the pellets/granules will normally be </=30% (w/w). The product will have a spherical/spheroidal form when the starting material has such a form.

(ii) Extrusion of a moistened mass that contains active substance and an appropriate plastifying binder (e.g. 10–50% microcrystalline cellulose or methyl cellulose), followed by rounding the extrudate on a rotating disc.

(iii) Coating of crystals of active substance with auxiliary substances like suitable polymers. The geometric shape of the ultimate pellets/granules is determined by the geometric shape of the crystals.

(iv) Atomization and subsequent cooling of a melt containing the drug substance.

In order to optimize and control the sustained release properties, the granules should preferably be spherical (pellets) and have a uniform size. Niro Atomizer has introduced a novel method for preparing pellets (U.S. Pat No. 5,030,400 that is hereby incorporated by reference). By their process, pellets are prepared in a high shear mixer by spraying an aqueous binder solution onto finely divided solid material during continued mixing. A controlled growth of the pellets is achieved by carefully controlling the liquid saturation of the moist granules during the process. The process requires a high energy input.

It has recently been demonstrated that pelletization can be achieved in high shear mixers from powdery mixtures containing active substances and wax-like hydrophilic melting binders (i.e. polyethylene glycols) (PCT application PCT/SE91/00690 (now U.S. Pat. No. 5,476,677) and T. Schaefer et al, Drug Development and Industrial Pharmacy 16 (1990) 1249–77)). Polyethylene glycol liquefies during the process due to the development of heat caused by the agitation. This latter process is usually classified as melt granulation or thermoplastic granulation. Pellets within the size range given above and with a narrow size distribution and a high content of active drug substance have been achieved.

Processes for the manufacture of sustained release formulations (granules/pellets as well as tablets) using wax-like binders are well-known (U.S. Pat. No. 4,013,784 and U.S. Pat. No. 4,132,753 granules; U.S. Pat. No. 4,935,246 coating of granules; Ghali et al, Drug Dev Ind Pharm 15(9) (1989) 1311–1328 extrusion and spheronization).

DIFFICULTIES ASSOCIATED WITH MANUFACTURE OF DELAYED RELEASE GRANULES

A major problem related to the manufacture of granules and pellets is to control their release properties. Granules/pellets present an extremely large surface and a high release rate potential compared to the corresponding tablet formulations. Due to the large surface area granules/pellets and multi unit dose formulations will normally give a considerable burst effect, i.e. an immediate initial release of a significant proportion of the drug substance, because rapid dissolution of the solid drug particles positioned in the surfaces of the granules/pellets. The burst effect is dependent on the water solubility of the active substance (drug).

A sustained release from granules/pellets and tablets is often affected by a simultaneous release or degradation of binder and filler material.

THE OBJECTIVES OF THE INVENTION

The main objective of the invention has been to devise a simple and effective process for the manufacture of pellets that contain a drug and have defined and sustained release properties.

Another objective has been to manufacture pellets that have a low or no significant burst release of the drug.

A third objective has been to design a pellet manufacturing process with general applicability for different drugs and release characteristics.

A fourth objective has been to provide pellets complying with the characteristics given further below in this specification.

THE INVENTION

The invention aims at counteracting the disadvantages of the prior art granules/pellets and is a method for the manufacture of sustained release pellets containing a drug. The invention also encompasses multiple unit dose formulations containing the pellets. The method comprises pelletizing a mixture containing the drug in finely divided form together with a binder and other auxiliary substances, such as fillers etc.

The characteristic features of the method and benefits of the pellets produced are mainly attributed to the pelletization step. The inventive method is thus primarily characterized in that (a) said binder is particulate and contains one or more water-insoluble wax-like binder substances with a melting point above 40° C., and (b) said pelletization is performed by mechanically working, in a high shear mixer, the mixture under input of a sufficient amount of energy for the binder to melt and the pelletization to take place.

The pellets may after having been formed be subjected to sieving in order to remove pellets of sizes above and below predetermined limits, and then portioning the remaining pellets into dose units. By the term dose unit is intended the amount of pellets placed in a capsule, tablet, sachet, blister pack etc.

A general description of suitable high shear mixers is given in U.S. Pat. No. 5,030,400 that is incorporated by reference. Normally they are round-bottomed or flat-bottomed bowls with a mixer device containing a designated impeller or mixing blade rotating about a central shaft close to the bottom and possibly also following the lower portion of the lateral walls of the bowls. In addition these mixers may also have a so-called chopper, i.e. fast rotating arms or knives projecting into the bowl. In order to provide the appropriate energy input to the agitated mass, the rotation speed of the impeller is normally adjustable to more than 100 rpm and of the chopper to more than 1500 rpm. The upper limit of the rotation speed for the impeller is dependent on the production volume, e.g. to be less than 2000 rpm for laboratory scale mixers and less than 800 rpm for production scale mixers. For the chopper the rotation speed is usually less than 3000 rpm. In addition the bowl may have means for external heating or cooling.

In order to control the pelletization, the inner surface of the bowl should have a low adhesion for the agitated mixture. Thus in the most preferred variants of the invention the inner walls of the bowl, the impeller and any other means being in contact with the agitated mass must be coated with an inert polymer having low adhesion for the binder, drug etc. It has been found that polyfluorethylene polymers (Teflon) of the appropriate wear resistance are close to perfect. Too low wear resistance will mean that the inappropriate adhesion properties will appear too soon.

Normally, a high shear mixer will provide the efficient energy input by mechanically working the mixture, meaning that external heating is not necessary. Improper heating may in many cases adversely affect the pelletization process. The ultimate result of the granulation process is particles of spherical or spheroidal shape (pellets) and uniform size in high yields. The drug becomes embedded in a matrix of wax-like substances and, optionally, together with other excipients. For instance the method can be controlled to the formation of pellets having a predetermined mean diameter within 0.2–2.5 mm, preferably 0.5–2.0 mm, and with at least 75% (w/w, yield) of the pellets within +/−25% or within +/−50%, preferably within +/−0.35%, of said predetermined mean diameter. Thus the inventive pellets may be obtained in uniform size with a geometric standard deviation of 1.4 or less. The spheres formed are often characterized by a low porosity that increases inwards the spheres. The total pore volume may be beneath 8% or even beneath 5% in relation to the volume of the spheres.

The drug may be soluble or insoluble in water, with preference for drugs having a solubility that is higher than 1:100 in water buffered to pH=7. Its melting point should be above the melting point for the binder, for instance more than 20°–30° C. above the melting point of the binder. In most cases the melting point of the drug is above 120° C. or even above 140° C. The drug shall be in solid particulate form at the temperature used in the inventive process. The particle size of the drug may be within the range contemplated for conventional granulation/pelletization processes, which means within 1–200/um, in particular 5–100/um. Thus, the process is applicable even to cohesive drug substances. Depending on the potency of the drug, the release rate desired and the process parameters used for manufacturing the pellets, the drug content may vary between 1–90% of the final pellets (w/w), although in the normal situation the drug content is 20–80 % (w/w).

The present inventive process is of potential use for any drug that is to be administered orally in order to maintain predetermined blood levels throughout the day. Thus the drug may be bronchodilating, anti-inflammatory, antineoplastic, cytostatic, anti-conceptive, anti-coagulative, pain-releasing anesthetics etc and used in different fields such as urology, gynecology, autoimmunity, gastro enterology etc. Specific drugs to be mentioned are paracetamol, acetyl salicylic acid, morphin, theophylline, proxophylline, tranexamic acid, steroid hormones, omeprazol etc including, where appropriate, corresponding pharmaceutically and physiologically acceptable salts and prodrugs thereof, such as esters, which salts and prodrugs shall give rise to therapeutic effects.

Wax-like binder substances, including waxes as such, are well known in the galenic field and comprise natural, semisynthetic or synthetic plastic substances. The present invention may utilize wax-like substances that are termoplastic with melting points above +40° C., preferably above +45°, and below +120° C. such as below +110° C. Preferably, good wax-like thermoplastic substances have melting points 70 °–100° C. In case a wax-like substance of a melting point that is higher than 120°is possible to liquefy by simple mechanical working that substance may also be useful in the present invention.

The binder may consist of one or more water-insoluble wax-like thermoplastic substance(s) possibly mixed with one or more wax-like thermoplastic substances being less hydrophobic than said one or more water-insoluble wax-like substances. To meet the desire for constant release, it is believed that the individual wax-like substances in the binder should be substantially non-degradable and insoluble in gastrointestinal fluids under the relevant time frame and at least under the initial release phase.

Useful water-insoluble wax-like substances may have a water-solubility that is lower than about 1:5000 (w/w)

Potential binder substances are preferably water-insoluble with more or less pronounced hydrophilic and/or hydrophobic trends. Specifically the wax-like substance may comprise fatty alcohols, fatty acids esters, fatty acid glycerides (mono-, di- and triglycerides), hydrogenated fats, hydrocarbons, normal waxes and hydrophobic and hydrophilic polymers having hydrocarbon backbones. A particularly useful hydrophobic water-insoluble wax-like substance is microcrystalline wax, e.g. Petrolite 195 (Petrolite Corp., U.S.A.). Particularly useful wax-like substances with different degrees of hydrophilicity/hydrophobicity/lipophilicity are bees wax (pronounced lipophilic), glyceromonostearate (GMS), and sorbitan esters (for example Span 60 having a melting point of 50° C. and a HLB of 4.7).

In order to select wax-like substances having good thermoplastic pelletization properties, it is important to check them empirically as outlined in our experimental part. This depends on the knowledge with regard to critical parameters of wax-like substances being deficient for the time being. However, it is believed that their hydrophobic/hydrophilic balance may be of importance as well as their viscosity and contact angle. One should look for suitable thermoplastic wax-like substances among those having viscosity beneath 1000 cps at the pelletization temperature, e.g at 70° C., and a hydrophilic-lipophilic balance (HLB-value) lower than 5, preferably lower than 3.

In total the binder content may be in the range 10–90% (w/w/), such as 10–50% (w(w) with a preferred upper limit of 30% or 40% (w/w). In particular the preferred range is 15–25% (w/w).

The auxiliary substances (except the binder) used in connection with the invention are those commonly used in the field. For instance conventional fillers may be included, such as calcium hydrogen phosphate, lactose etc of the proper quality. Examples of other auxiliary substances are buffering substances and release rate increasing substances.

The pellets of the present invention is primarily intended for oral ingestion and passage through the gastrointestinal channel. The pH environment of ingested pellets changes during the passage. Because of this change, the solubility of the drug particles may change as well as the solubility and stability of the filler and binder matrix. The effect of the varying solubility during passage through the gastrointestinal tract can be counteracted by addition of auxiliary substances having an acid or a basic character contributing to a buffered "micro-environment" in the inventive pellets. This is a previously well known means to adjust the rate of release from tablets and granules. The same principle is applicable to the pellets of the present invention. Accordingly, basic substances like magnesium hydroxide and acidic substances like tartaric acid may be included. The selection between a basic or an acidic buffering substance depends on the drug and where in the gastrointestinal tract the drug is to be released. In many cases fillers having the appropriate buffering capacity may act as a buffering substance.

The present process as such does not prohibit a burst effect. However, the burst effect may easily be counteracted by reduction of the pellet surface concentration of solid drug particles. This can be achieved by addition at a late stage of the pelletization process of a water-insoluble hydrophobic wax-like thermoplastic substance as defined above. This additional wax-like substance is added as a finely divided powder at a process temperature which causes melting of the substance and coating of the produced pellets. The wax-like substance used in this coating step may be between 1–10% of the total mount of ingredients added. Accordingly, pellets may be produced having an approximately constant release even from the very initial release stage. Pellets produced according to the invention may also be coated in conventional ways.

In connection with previously known granules and tablets with sustained release, it is known that certain powder substances, such as talc, when located in the surface of sustained release granules or tablets have an increasing effect of the overall release rate. One mode of the invention is therefore to balance the binder so that slightly overwetted pellets are formed during the mechanical working, and then, as out-lined by the prior art, in a second step add a rate increasing compound as a fine powder and continue working so that the surfaces of the pellets become covered with the powder.

Dose units of the inventive pellets may be administered in those forms that are known for multiple unit dose formulations, for instance as capsules (either enteric coated or non-coated), suspensions, sachets, tablets etc.

The invention is illustrated in the experimental part and is defined in the appending claims that are an integral part of the specification.

EXPERIMENTAL PART

Manufacture of the pellets

As pelletizing equipment a Pellmix pl ⅛ (Niro Atomizer, Denmark) was used. The filler, drug and solid binder consisting of wax-like binder substances were transferred to the mixing bowl which may have been preheated. The powders were mixed at approximately 1200 rpm until the product temperature reached 90° C. and the impeller speed was then lowered to 500 rpm for calcium hydrogen phosphate-based formulations and to 1000 rpm for lactose-based formulations. The products were run for an additional period of 5–15 minutes allowing the pellets to form. Finally the products were emptied out of the mixer, tray cooled and fractioned.

Binder substances used in our experiments were: Glyceryl monostearate (=GMS), stearyl alcohol, stearic acid, triglycerid (Danske Sukkerfabrikker, Denmark), beeswax, microcrystalline wax (=MC-wax), all of which were wax-like and thermoplastic (MC-wax was Petrolite 195 (Petrolite Corp., U.S.A.))

The results of the release experiments are represented graphically in FIGS. 1–6.

FIG. 1: The effect of binder type on release of paracetamol.

Figure 2:
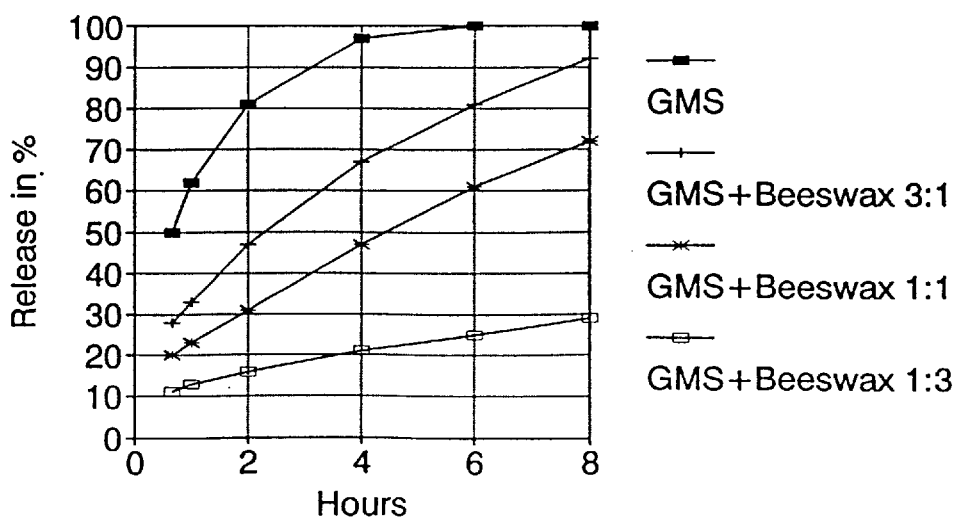

FIG. 2: The effect of binder composition on release of paracetamol.

Figure 3:
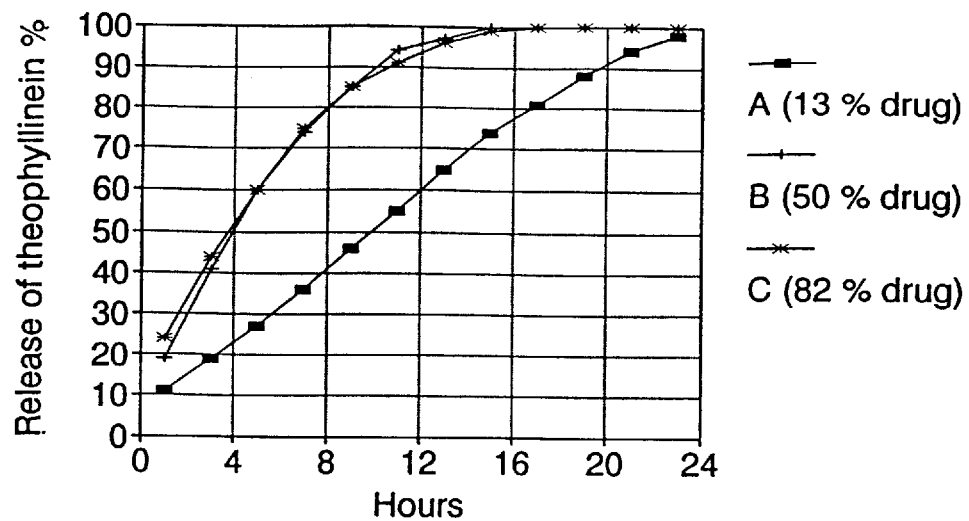

FIG. 3: The effect of drug content on theophylline release.

Figure 4:
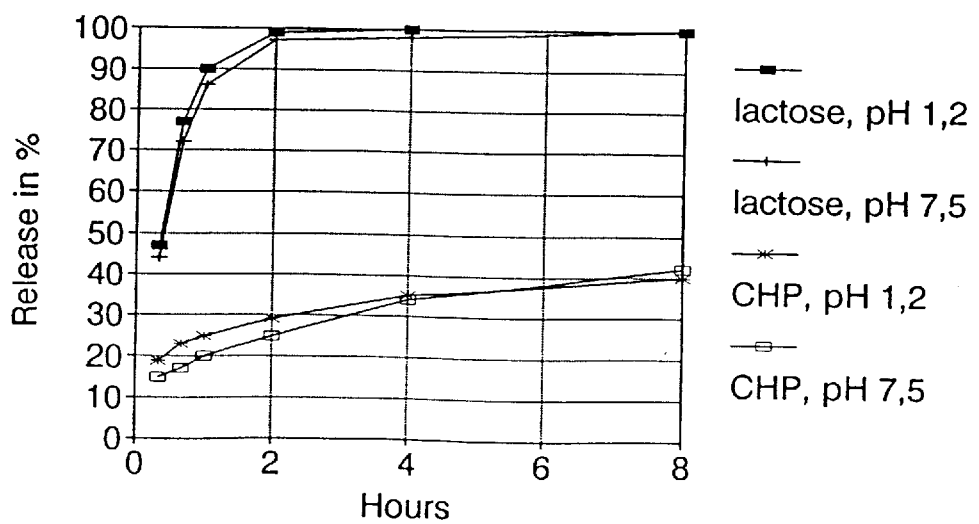

FIG. 4: The effect of pH and filler solubility on paracetamol release. CHP stands for calcium hydrogen phosphate ($CaHPO_4$).

Figure 5:
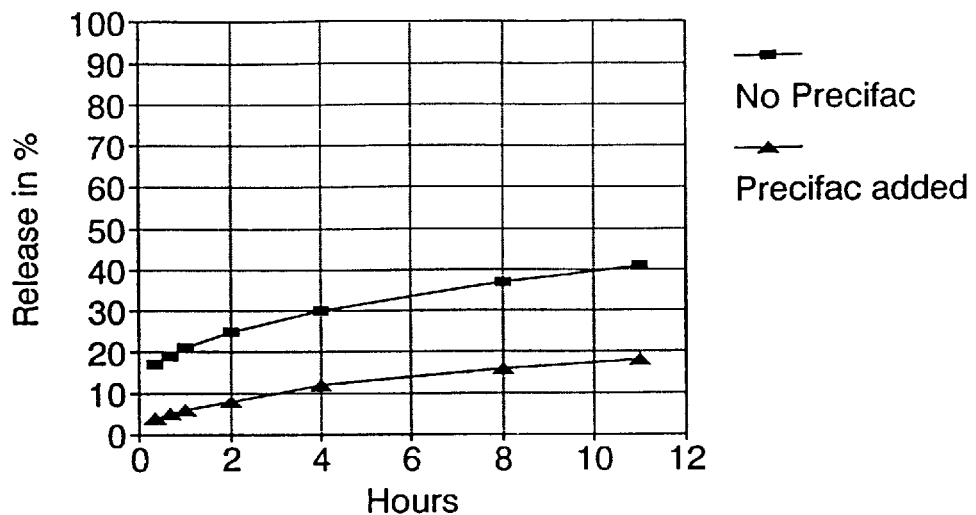

FIG. 5: The effect on paracetamol release of adding a meltable lipophilic powder.

Figure 6:
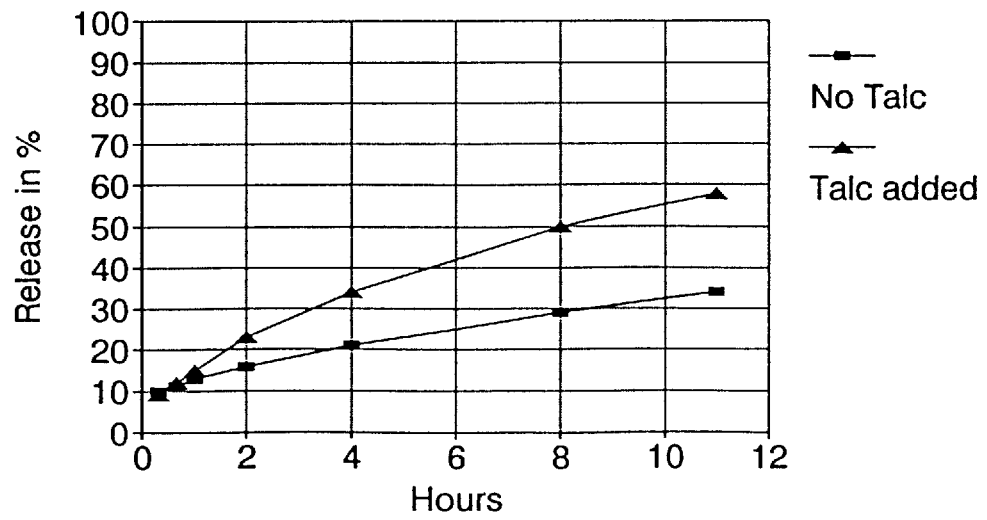

FIG. 6: The effect on paracetamol release on adding talc.

EXAMPLE 1. EFFECT OF BINDER TYPE

| Composition: | $CaHPO_4$ | 888 g |
| --- | --- | --- |
| | Paracetamol | 120 g |
| | Glyceryl monostearate (GMS) | 96 g |
| | Lipophilic binder substances | 96 g |

The release of the 1000/um–1400/um fractions of the products were measured in an USP dissolution apparatus. Basket rotational speed was 100 rpm and the medium was 1000 ml Simulated Gastric Fluid, no enzymes (pH: 1.2).

TABLE 1

Effect of binder type on release of paracetamol.

| | % Release | | | | | |
| --- | --- | --- | --- | --- | --- | --- |
| Hours | 0.66 | 1 | 2 | 4 | 6 | 8 |
| Binder: | | | | | | |
| GMS | 50 | 62 | 81 | 97 | 100 | 100 |
| GMS + Stearyl alc. | 29 | 35 | 49 | 68 | 79 | 87 |
| GMS + Stearyl acid | 27 | 32 | 43 | 62 | 78 | 91 |
| GMS + Triglycerid DS | 19 | 24 | 38 | 60 | 74 | 86 |
| GMS + Beeswax | 20 | 23 | 31 | 47 | 61 | 72 |
| GMS + MC-wax | 19 | 21 | 26 | 34 | 41 | 47 |

The combination of GMS with lipophilic binders made it possible to modify the release rate. The GMS/MC-wax mixture showed relatively good sustained release properties (FIG. 1).

EXAMPLE 2. EFFECT OF THE BINDER COMPOSITION

| Composition: | CaHPO$_4$ | 888 g |
|---|---|---|
| | Paracetamol | 120 g |
| | Binder | 192 g |

The binder was either pure GMS, GMS/beeswax (3:1), GMS/beeswax (1:1) or GMS/beeswax (1:3).

Dissolution was measured as in Example 1.

TABLE 2

Effect of binder composition

| | % Release | | | | | |
|---|---|---|---|---|---|---|
| Hours | 0.66 | 1 | 2 | 4 | 6 | 8 |
| Binder: | | | | | | |
| GMS | 50 | 62 | 81 | 97 | 100 | 100 |
| GMS + Beeswax 3:1 | 28 | 33 | 47 | 67 | 81 | 92 |
| GMS + Beeswax 1:1 | 20 | 23 | 31 | 47 | 61 | 72 |
| GMS + Beeswax 1:3 | 11 | 13 | 16 | 21 | 25 | 29 |

As shown in table 2 and FIG. 2 it was possible to modify the release profile by varying the composition of the binder.

EXAMPLE 3. EFFECT OF DRUG CONTENT

| Composition: | A | B | C |
|---|---|---|---|
| Theophylline | 150 g | 477 g | 700 g |
| CaHPO$_4$ | 850 g | 323 g | 0 g |
| GMS | 96 g | 80 g | 76 g |
| MC-wax | 89 g | 75 g | 71 g |

The release rate was measured as in example 1.

TABLE 3

Effect of drug content

| | % Release | | | | | |
|---|---|---|---|---|---|---|
| Hours | 1 | 3 | 5 | 7 | 9 | 11 |
| Binder: | | | | | | |
| Composition A | 11 | 19 | 27 | 36 | 46 | 55 |
| Composition B | 19 | 41 | 60 | 74 | 85 | 94 |
| Composition C | 24 | 44 | 60 | 75 | 85 | 91 |

As shown in table 3 and FIG. 3 the drug content could make a total of up to approximately 80–90% of total pellet weight.

EXAMPLE 4. EFFECT OF FILLER AND pH OF THE DISSOLUTION MEDIUM

| Composition D: | CaHPO$_4$ | 880 g |
|---|---|---|
| | Paracetamol | 120 g |
| | GMS | 99 g |
| | MC-wax 195 | 93 g |
| Composition E: | Lactose 450 mesh | 880 g |
| | Paracetamol | 120 g |
| | GMS | 99 g |
| | MC-wax 195 | 93 g |

The release of paracetamol into simulated gastric fluid (pH 1.2) and simulated intestinal fluid (pH 7.5) was measured in analogy with the method given in example 1.

TABLE 4

Effect of filler and pH of the dissolution medium

| | % Release (pH 1.2) | | | | | | |
|---|---|---|---|---|---|---|---|
| Hours | 0.33 | 0.66 | 1 | 2 | 4 | 6 | 8 |
| Composition D | 19 | 23 | 25 | 29 | 35 | 40 | 45 |
| Composition E | 47 | 77 | 90 | 99 | 100 | 100 | 100 |

| | % Release (pH 7.5) | | | | | | |
|---|---|---|---|---|---|---|---|
| Hours | 0.33 | 0.66 | 1 | 2 | 4 | 6 | 8 |
| Composition D | 15 | 17 | 20 | 25 | 34 | 42 | 48 |
| Composition E | 44 | 72 | 86 | 97 | 98 | 100 | 100 |

As shown in table 4 and in FIG. 4, the release rate was highly dependent on the solubility of the filler (CaHPO$_4$, or lactose). The pH of the medium has only a minor effect on the release of paracetamol from the products D and E.

EXAMPLE 5. ADDITION OF A MELTABLE LIPOPHILIC POWDER

| Composition: | F | G |
|---|---|---|
| CaHPO$_4$ | 648 g | 648 g |
| Paracetamol | 360 g | 360 g |
| GMS | 48 g | 48 g |
| Beeswax | 144 g | 144 g |
| Precifac | approx. | 5 g |

The portion of Precifac (cetyl palmitate, Gatefosse, France, composition G) was added at the end of the pelletization phase whereafter the mixture was run for additional 30 seconds.

The release into simulated gastric fluid (pH 1.2) was measured in analogy with the method given in example 1.

TABLE 5

Effect of adding a meltable lipophilic powder

| | % Release in simulated gastric fluid | | | | | |
|---|---|---|---|---|---|---|
| Hours | 0.33 | 0.66 | 1 | 2 | 4 | 8 | 11 |
| Composition F | 17 | 19 | 21 | 25 | 37 | 41 | 48 |
| Composition G | 4 | 5 | 6 | 8 | 12 | 16 | 18 |

As shown in table 5 and FIG. 5, a substantial decrease in initial as well as in overall release rate was achieved by adding a meltable lipophilic powder (Precifac).

EXAMPLE 6. EFFECT OF THE ADDITION OF TALC

| Composition | H | I |
|---|---|---|
| CaHPO$_4$ | 888 g | 888 g |
| Paracetamol | 120 g | 120 g |
| GMS | 48 g | 48 g |
| Beeswax | 144 g | 144 g |
| Talc |  | 5 g |

The talc portion was added after the pelletization phase for composition I, whereafter the mixture was worked for additional 30 seconds. Talc addition increased the overall release rate without increasing the initial release.

The release of paracetamol in simulated gastric fluid (pH 1.2) was measured in analogy with the method given in example 1.

TABLE 6

Effect of adding talc

| | % Release (pH 1.2) | | | | | | |
|---|---|---|---|---|---|---|---|
| Hours | 0.33 | 0.66 | 1 | 2 | 4 | 8 | 11 |
| Composition H | 10 | 11 | 13 | 16 | 21 | 29 | 34 |
| Composition I | 9 | 12 | 15 | 23 | 34 | 50 | 58 |

As shown in table 6 and FIG. 6, the addition of talc increased the overall release rate without increasing the initial release rate.

It is claimed:

1. A process for the manufacture of sustained release pellets, comprising:

pelletizing a mixture containing a drug in finely divided form having a particle size of 1–200 μm and a binder, characterized in that
   (a) said binder is particulate and comprises one or more water-insoluble wax-like binder substances with a melting point above 40° C., and
   (b) said pelletization step is performed by mechanically working said mixture, in a high shear mixer, under the input of a sufficient amount of energy for the binder to melt and pelletization to take place.

2. A process for the manufacture of sustained release pellets according to claim 1, characterized in that said pellets after being formed
   (i) are sieved thereby removing pellets of sizes above and below predetermined limits, whereafter
   (ii) the remaining pellets are portioned into dose units.

3. A process for the manufacture of sustained release pellets according to any one of claims 1 or 2 characterized in that a further portion of a wax-like binder substance is added to the mixture after the pellets have been formed whereupon the working of the mixture is continued so that the wax-like substance of the further portion melts and coats the pellets.

4. A process for the manufacture of sustained release pellets according to any one of claims 1 or 2 characterized in that the drug is intended for the treatment of a disease within the field of urology, gynecology, autoimmunity or gastroenterology.

* * * * *